US005683463A

United States Patent [19]
Godefroy et al.

[11] Patent Number: 5,683,463
[45] Date of Patent: Nov. 4, 1997

[54] INTERSOMATIC VERTEBRAL COLUMN IMPLANT

[75] Inventors: Jean Godefroy, Ayze; Claude Laville; Raymond Roy-Camille, both of Paris, all of France

[73] Assignee: Advanced Technical Fabrication, Marignier, France

[21] Appl. No.: 281,243

[22] Filed: Jul. 27, 1994

[30] Foreign Application Priority Data

Aug. 6, 1993 [FR] France ................................ 93 09835

[51] Int. Cl.$^6$ .................................................. A61F 2/44
[52] U.S. Cl. .................................................. 623/17
[58] Field of Search ................ 623/11, 16, 17, 623/20; 606/53, 60, 61, 63; 433/173, 174

[56] References Cited

U.S. PATENT DOCUMENTS

| | | | |
|---|---|---|---|
| 4,349,921 | 9/1982 | Kuntz . | |
| 4,501,269 | 2/1985 | Bagby . | |
| 4,645,453 | 2/1987 | Niznick | 433/173 |
| 4,936,848 | 6/1990 | Bagby . | |
| 5,015,247 | 5/1991 | Michelson | 623/17 |
| 5,338,197 | 8/1994 | Kwan | 433/174 |
| 5,489,308 | 2/1996 | Kuslich et al. | 623/17 |

FOREIGN PATENT DOCUMENTS

| | | | |
|---|---|---|---|
| 0307241 | 3/1989 | European Pat. Off. . | |
| 0369603 | 5/1990 | European Pat. Off. | 623/17 |
| 87/07827 | 12/1987 | WIPO . | |
| 89/12431 | 12/1989 | WIPO . | |

*Primary Examiner*—Robert A. Clarke
*Attorney, Agent, or Firm*—Ratner & Prestia

[57] ABSTRACT

The hollow tubular implant of the invention comprises an internal cavity delimited by a peripheral wall open at its first end and having a generally circular cross-section external surface. Two side surfaces are solid and top and bottom surfaces have communicating holes in them. Annular external ribs prevent retrograde movement and rotation of the implant when inserted between two adjacent vertebrae. The implant achieves good fastening together of the two vertebrae and fusion thereof by means of a bone graft inserted in the implant before fitting.

17 Claims, 4 Drawing Sheets

INTERSOMATIC VERTEBRAL COLUMN IMPLANT

BACKGROUND OF THE INVENTION

1. Field of the Invention

The present invention concerns hollow tubular intersomatic implants for stabilization of the vertebral column designed to form a plug to be inserted into prepared grooves in the facing surfaces of two adjacent vertebrae to maintain a constant disk space.

2. Description of the Prior Art

A hollow tubular intersomatic implant of this kind is described in document U.S. Pat. No. 4,501,269, for example. It comprises an interior cavity delimited by a peripheral wall open at least at a first end. Also included are top and bottom openings providing communication between the exterior and the interior of the implant and enabling direct contact between the vertebrae and a spongy bone graft inserted into the implant. This produces an intersomatic vertebral graft.

Document WO-A-89 12431 describes another device comprising a cylindrical cage having holes distributed over its lateral surface and an exterior helical thread for screwing it into place.

These devices have been found ineffective for bonding together two successive vertebrae as the size of the holes is necessarily limited and there is insufficient immobilization against rotation.

Document EP-A-0 307 241 describes another implant in the form of a parallelepiped-shape cage. The longitudinal edges of a cage of this kind may rub on the spinal cord or the spinal nerve roots during insertion of the implant between the adjacent vertebrae.

Another prior art implant is in the form of a cylindrical cage delimited by four columns joining two ends of the cage. The columns are disposed parallel to the facing surfaces of the vertebrae. An implant of this kind is ineffective at restoring normal curvature of the spine because of the insufficient mechanical stiffness of its structure.

The present invention solves the problem of defining a new intersomatic implant structure which very significantly reduces the risk of nervous lesions during fitting and provides better location and better immobilization of the implant against rotation between the vertebrae and increased mechanical strength and good bone attachment to facilitate fusion of two adjacent vertebrae.

The invention is also directed to solving the problem of correcting the intervertebral angle by making the implant a particular shape for restoring normal curvature of the lumbar spine.

SUMMARY OF THE INVENTION

To achieve these and other objects, the intersomatic implant of the invention has a peripheral wall which comprises:

a generally circular cross-section external surface, (1) two solid side surfaces, and (2) top and bottom surfaces having said communicating holes in them, and at least one annular external rib to prevent retrograde movement.

In a preferred embodiment of the invention the peripheral wall further comprises at least one external anti-rotation relief adapted to be embedded in the bone of a vertebra to oppose rotation of the implant around its longitudinal axis.

The peripheral wall is preferably either generally frusto-conical in shape or ovoidal in shape with truncated longitudinal ends, the larger base consisting of the surface at the first end and the smaller base consisting of the surface at the second end.

In an advantageous embodiment of the invention the side surfaces include a flat portion on their outside surfaces and have no annular external ribs.

Other objects, features and advantages of the present invention emerge from the following description of specific embodiments of the invention given with reference to the accompanying figures.

DETAILED DESCRIPTION OF THE PREFERRED EMBODIMENTS

Figure 1:
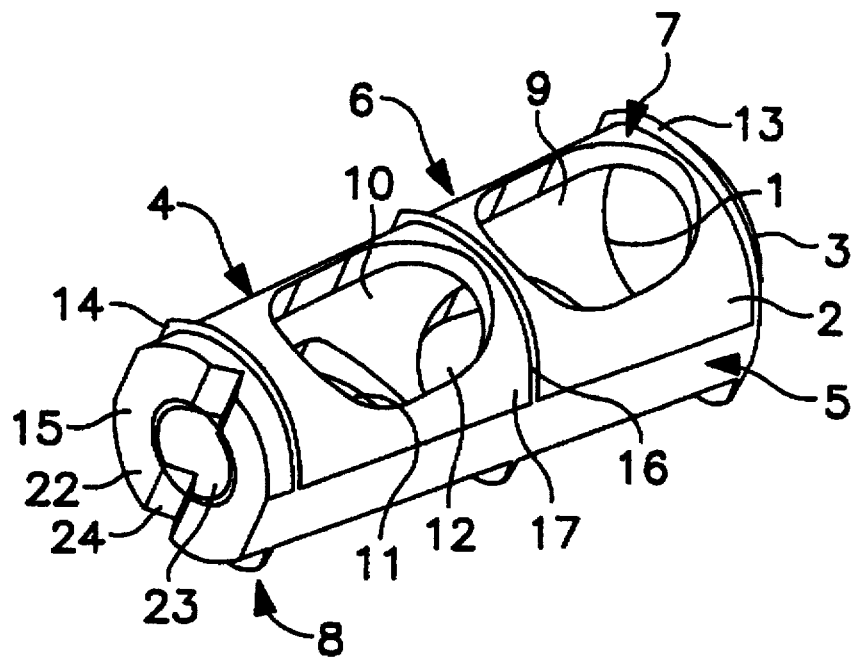
FIG. 1 is a three-quarter top view in perspective of a first embodiment of an intersomatic implant of the present invention.
Figure 2:
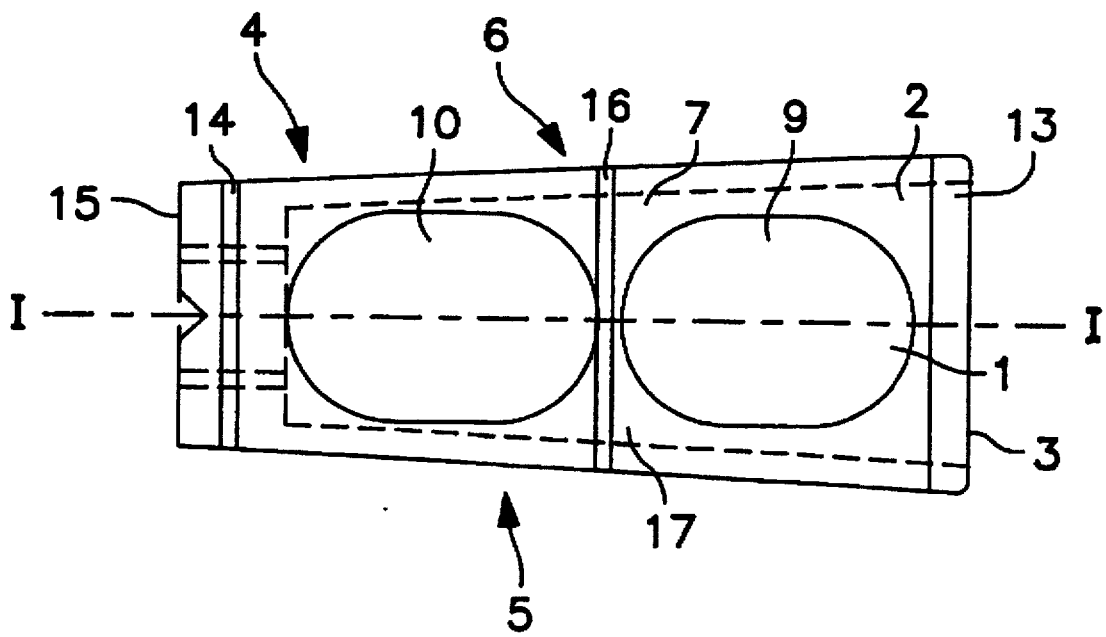
FIG. 2 is a top view of the implant from FIG. 1.

Referring to the figures, the intersomatic implant of the invention is a hollow tubular member having a longitudinal axis I—I and made from metal or a rigid synthetic material, for example, comprising an interior cavity 1 delimited by a peripheral wall 2 open at least at a first end 3.

The peripheral wall 2 has a generally circular section exterior surface 4. This exterior surface 4 is made up of two solid side surfaces 5 and 6. The exterior surface 4 also has top and bottom surfaces 7 and 8 with communicating holes in them. The top surface 7 has two communicating holes 9 and 10 in it and the bottom surface 8 has two communicating holes 11 and 12 in it, for example.

The peripheral wall 2 further comprises at least one annular external rib to prevent retrograde movement, for example the rib 13 near the first end 3.

In the embodiments shown the implant comprises a first annular external rib 13 near its first end 3, a second annular external rib 14 near its second end 15 and an intermediate annular external rib 16 in an intermediate area 17 of the peripheral wall 2 in which there are no communicating holes.

As shown in the embodiment represented in FIGS. 6 to 9, the annular external ribs 13, 14 and 16 are preferably toothed to prevent both axial movement in translation and rotation of the implant, the teeth becoming embedded in the vertebrae.

As an alternative to this, one or more longitudinal ribs projecting from the exterior surface of the peripheral wall 2 can be provided. These anti-rotation means are more difficult to manufacture, however, than teeth on annular external ribs.

In all of the embodiments, the communicating holes 9, 10, 11 and 12 are advantageously oblong holes whose length is slightly less than half the length of the implant and whose width is substantially equal to the diameter of the implant.

It is to be understood that an implant of the invention can comprise one, two or three ribs, or a larger number of annular external ribs.

Figure 3:
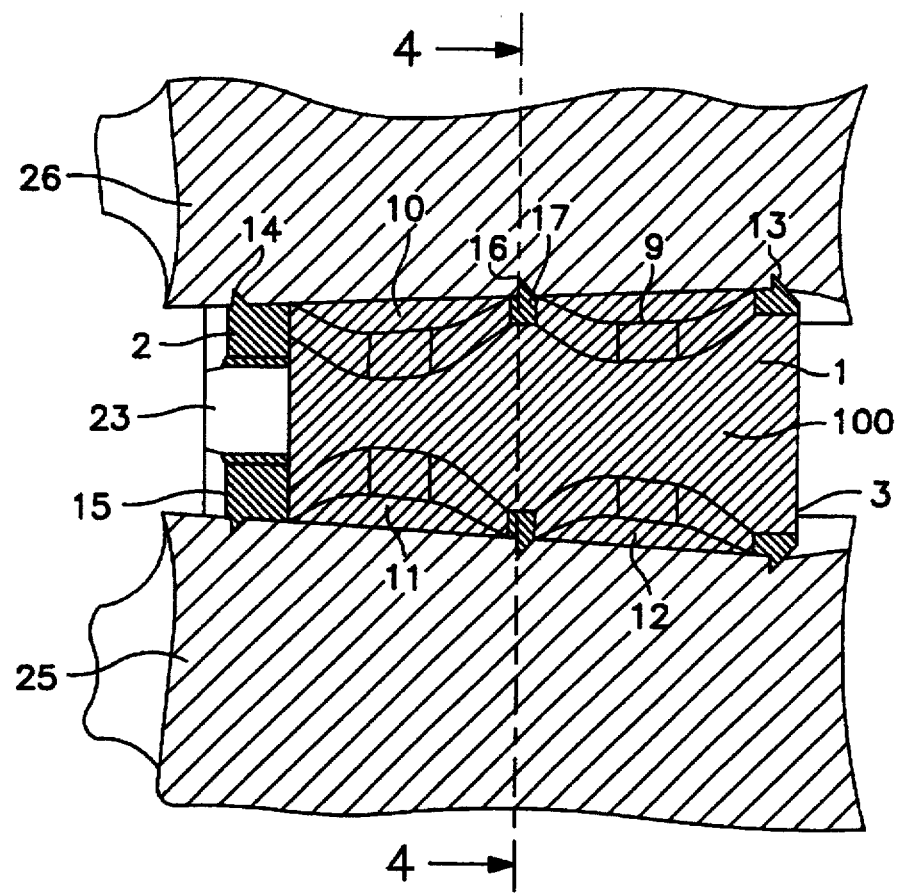
FIG. 3 is a side view in longitudinal section showing the implant from FIG. 1 in position between two vertebrae.
Figure 5:
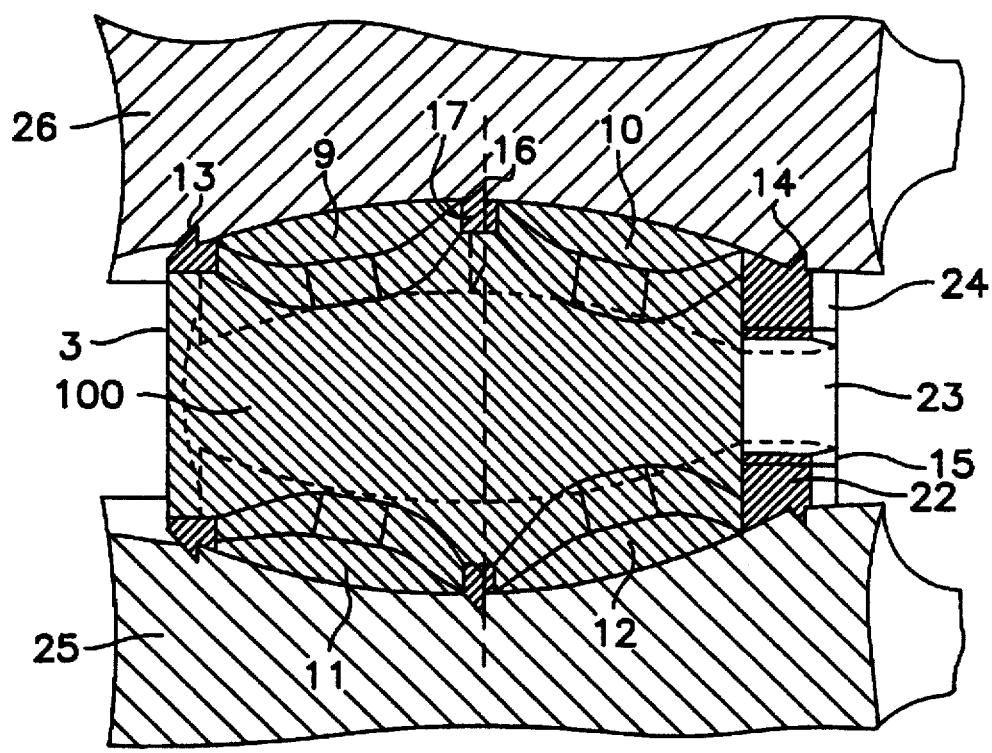
FIG. 5 is a side view in longitudinal section showing a generally ovoidal-shape implant with truncated longitudinal ends.
Figure 6:
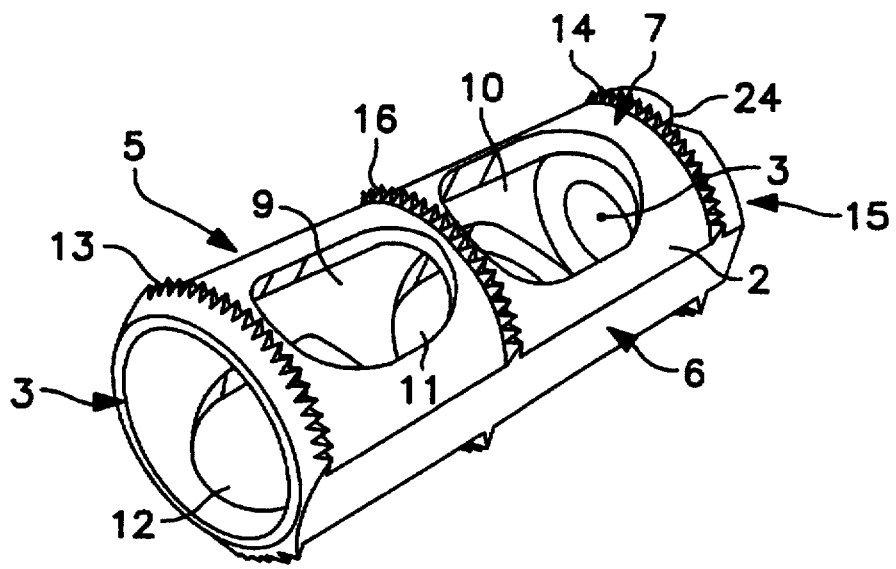
FIG. 6 is a three-quarter top view in perspective of a second embodiment of implant of the invention.
Figure 7:
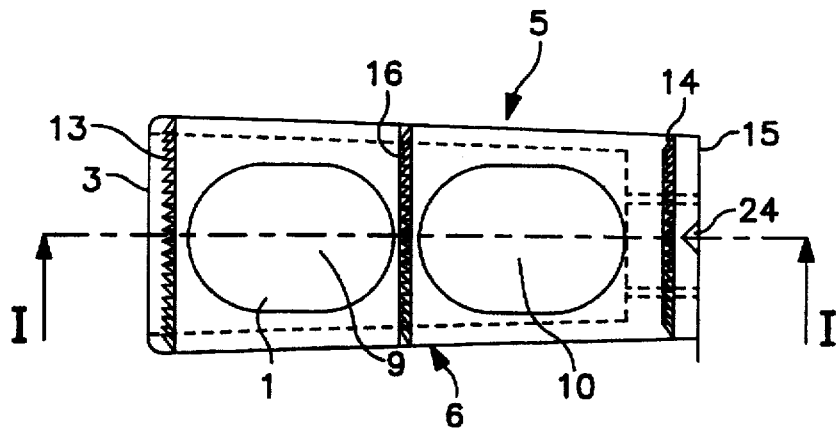
FIG. 7 is a top view of the implant from FIG. 6.
Figure 8:
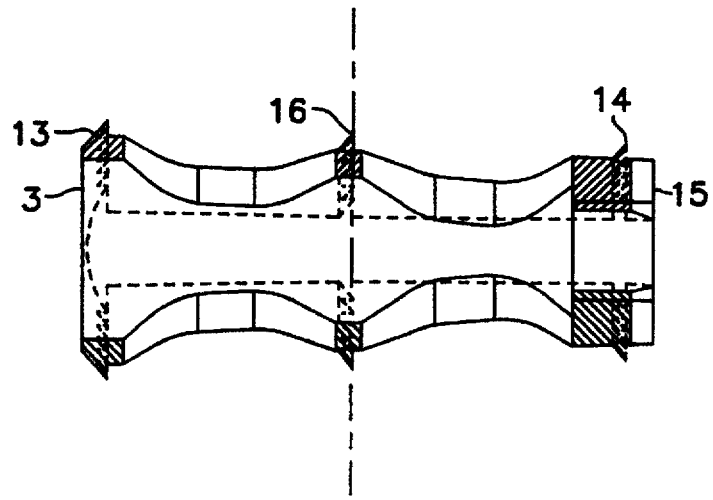
FIG. 8 is a view in longitudinal section of the implant from FIG. 6.
Figure 9:
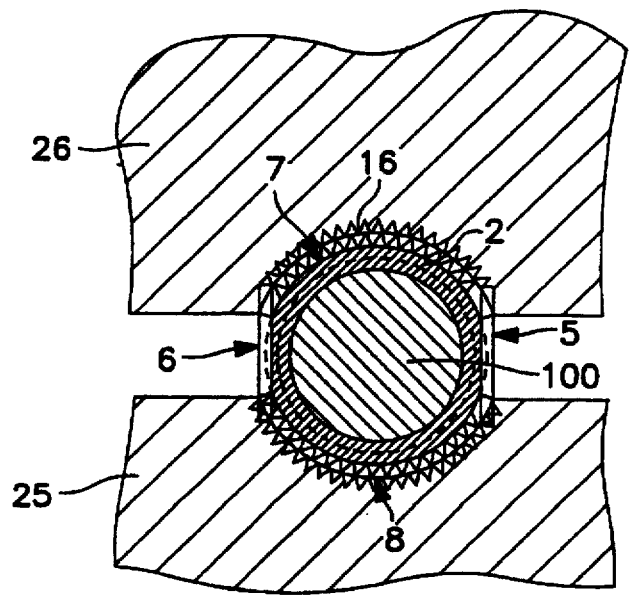
FIG. 9 is a view in transverse section of the implant from FIG. 6.

Referring to FIGS. 3, 5 and 8 in particular, each annular external rib 13, 14 or 16 preferably has an asymmetric sawtooth shape transverse cross-section preventing movement of the implant in the direction towards the second end 15.

In the embodiments of FIGS. 1 to 3 and 6 to 8 the peripheral wall 2 has a generally frustoconical external shape, the larger base consisting of the surface at the first end 3 and the smaller base consisting of the surface at the second end 15. This kind of shape can restore and maintain the appropriate physiological angle between two adjacent vertebrae.

In the FIG. 5 embodiment, the peripheral wall 2 has a generally ovoidal external shape with truncated longitudinal ends forming a larger base at the first end 3 and a smaller base at the second end 15.

The ovoidal shape is chosen because it is a better fit to the anatomical shape of the vertebrae between which the implant is to be inserted. Before insertion of the implant, the grooves are given an appropriate longitudinal profile.

Figure 4:
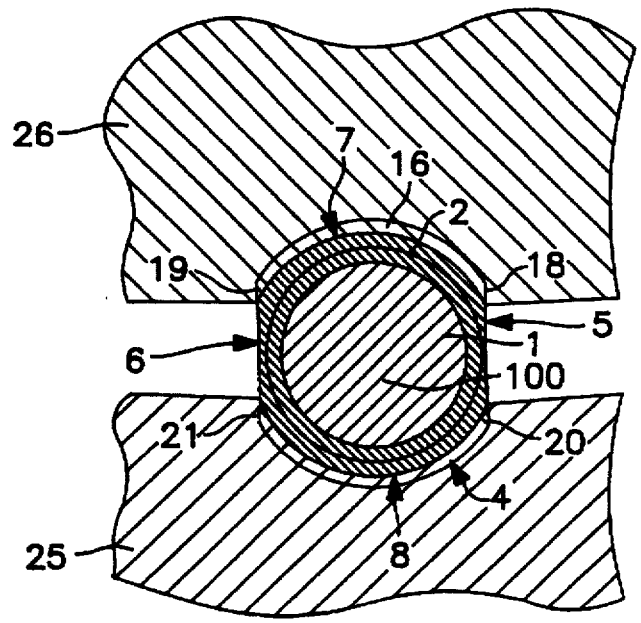
FIG. 4 is a view in transverse section on the line A—A in FIG. 3.

In the embodiments shown, the side surfaces 5 and 6 have no peripheral external ribs. Consequently, as seen more clearly in FIGS. 4 and 9, the annular external ribs are interrupted at each side surface 5 or 6. The peripheral rib 16, for example, includes two interruptions 18 and 19 at the top and two interruptions 20 and 21 at the bottom which prevent rotation of the implant when it is engaged between two adjacent vertebrae.

The side surfaces 5 and 6 can comprise a flat portion on the outside surface, as shown in FIGS. 1, 4, 6 and 9, this allows the quantity of material from which the implant is made to be slightly reduced. This flat portion occupies the entire length of the respective side surface.

The peripheral wall 2 is joined at its second end 15 to a transverse bearing wall 22. This transverse bearing wall 22 includes a threaded axial hole 23 so that an insertion tool aligned with the implant can be fitted to the latter.

The transverse bearing wall 22 further includes external reliefs, for example, a diametral groove or slot 24, for constraining the insertion tool and the implant to rotate together.

The external reliefs are preferably shaped to provide a visual means of indicating the angular position of the implant about its longitudinal axis I—I. A external relief structure in the form of a diametral groove or slot is one way to provide this means of visual indication of angular position. Among other things, this enables the implant to be positioned between two vertebrae so that the top and bottom surfaces 7, 8 are facing corresponding faces of the two adjacent vertebrae between which the implant is inserted.

FIGS. 3, 4, 5 and 9 show an implant of the invention in position between two adjacent vertebrae 25 and 26.

Before inserting the insert, a spongy bone graft 100 taken from elsewhere in the body of the patient is inserted into its interior cavity 1.

Before inserting the implant between the two vertebrae, grooves of appropriate cross-section are formed in the respective vertebrae, oriented sagittally to the longitudinal axis of the spine, the combination of the two grooves forming a substantially cylindrical housing whose cross-section is substantially equal to the size of the second end 15 of the implant. The two vertebrae 25 and 26 are then moved apart by appropriate means and the implant inserted axially into the two grooves, after which the vertebrae are released. The frustoconical shape of the implant imparts an appropriate angular orientation to the vertebrae 25 and 26, reproducing the normal morphological angle such as the normal curvature of the lumbar spine. The annular external ribs 13, 14 and 16 engage in the bone of the vertebrae 25 and 26 to prevent axial displacement of the implant. The ends 18 through 21 of the annular external ribs and the longitudinal ribs or teeth bear on the bone to prevent rotation of the implant about its longitudinal axis.

When the implant is fitted, the spongy bone graft 100 is in contact with the bone tissue of the lower vertebra 25 and the upper vertebra 26 so that these vertebrae are progressively fused together. The large size of the communicating holes 9, 10, 11 and 12 favors this by providing good contact between the enclosed graft 100 and the bone tissue of the two vertebrae 25 and 26.

The solid side surfaces 5 and 6 of the implant of the invention make the latter rigid so that it can withstand compression loads between the two vertebrae 25 and 26.

The generally circular cross-section of the implant avoids the risk of neurological lesion during insertion of the implant between the two vertebrae.

The present invention is not limited to the embodiments specifically described, but includes all variants and generalizations thereof within the scope of the following claims.

There is claimed:

1. A hollow tubular intersomatic implant for stabilization of the vertebral column, the implant comprising:

a peripheral wall having a longitudinal axis, and delimiting an internal cavity where the peripheral wall includes communicating holes to provide communication between the exterior and said internal cavity, the internal cavity having a height extending along the longitudinal axis which is larger than the diameter of the communicating holes, wherein the peripheral wall comprises:

(a) a generally circular cross-section external surface, (b) two solid side surfaces and top and bottom surfaces where the top and bottom surfaces include said communicating holes, and (c) at least one annular external rib to prevent retrograde movement where the annular external rib is substantially perpendicular to said longitudinal axis.

2. The implant according to claim 1 wherein said peripheral wall further comprises means for preventing rotation of the hollow tubular intersomatic implant.

3. The implant according to claim 1 wherein said peripheral wall is generally frustoconical or ovoidal with truncated longitudinal ends, where said peripheral wall has a first end and a second end where the first end is larger than the second end.

4. The implant according to claim 1 wherein said peripheral wall comprises respective annular external ribs positioned near a first end and near a second end of said peripheral wall.

5. The implant according to claim 4 further comprising an intermediate annular external ring in an intermediate area of said peripheral wall in which there are not communicating holes.

6. The implant according to claim 1 wherein said peripheral wall is joined at a second end to transverse bearing wall.

7. The implant according to claim 6 wherein said transverse bearing wall comprises a threaded axial hole for fitting an inserting tool.

8. The implant according to claim 1 wherein the peripheral wall comprises two annular external ribs and the communicating holes are formed between the two annular ribs.

9. A hollow tubular intersomatic implant for stabilization of the vertebral column, the implant comprising:

a peripheral wall having a longitudinal axis, and delimiting an internal cavity where the peripheral wall includes communicating holes to provide communication between the exterior and said internal cavity, the internal cavity having a height extending along the longitudinal axis which is larger than the diameter of the communicating holes, wherein the peripheral wall comprises:

(a) a generally circular cross-section external surface, (b) two solid side surfaces and top and bottom surfaces where the top and bottom surfaces include said communicating holes, and (c) at least one annular external rib to prevent retrograde movement where the annular external rib is substantially perpendicular to said longitudinal axis;

wherein said two solid side surfaces do not have annular external ribs.

10. The implant according to claim 9 wherein the two solid side surfaces have a flat surface portion.

11. A hollow tubular intersomatic implant for stabilization of the vertebral column, the implant comprising:

a peripheral wall delimiting an internal cavity where the peripheral wall includes communicating holes, wherein the peripheral wall comprises:

(a) a generally circular cross-section external surface, (b) two solid side surfaces and top and bottom surfaces where the top and bottom surfaces include said communicating holes, (c) at least one annular external rib to prevent retrograde movement; and (d) means for preventing rotation of the hollow tubular intersomatic implant, the rotation preventing means having at least one tooth projecting from at least one of said annular external ribs.

12. A hollow tubular intersomatic implant for stabilization of the vertebral column, the implant comprising:

a peripheral wall delimiting an internal cavity where the peripheral wall includes communicating holes and an end, wherein the peripheral wall comprises:

(a) a generally circular cross-section external surface, (b) two solid side surfaces and top and bottom surfaces where the top and bottom surfaces include said communicating holes, (c) at least one annular external rib to prevent retrograde movement, and (d) a threaded axial hole for fitting an inserting tool, and a transverse bearing wall joined to said end of said peripheral wall where the transverse bearing wall has a plurality of external relief means for preventing rotation of the inserting tool relative to the implant.

13. The implant according to claim 12 wherein said plurality of external relief means are further for visually indicating the angular position of the implant about a longitudinal axis of the implant.

14. The implant according to claim 13 wherein each of the plurality of external relief means has a V-shape.

15. The implant according to claim 12 wherein each of the plurality of external relief means has a V-shape.

16. The implant according to claim 12 wherein:

the peripheral wall has a longitudinal axis, and the annular external rib is substantially perpendicular to said longitudinal axis.

17. The implant according to claim 12 wherein said two solid side surfaces do not have annular external ribs.

* * * * *